United States Patent

Sakaguchi et al.

Patent Number: 5,246,704
Date of Patent: Sep. 21, 1993

[54] VAGINAL SUPPOSITORY

[75] Inventors: Minoru Sakaguchi, Tondabayashi; Norio Awata, Yamatokoriyama; Tsuneo Kawashima, Osaka; Hiroshi Nakagawa, Nagaokakyo, all of Japan

[73] Assignee: Kanebo, Ltd., Tokyo, Japan

[21] Appl. No.: 913,102

[22] Filed: Jul. 14, 1992

Related U.S. Application Data

[63] Continuation of Ser. No. 468,309, Jan. 22, 1990, abandoned.

[30] Foreign Application Priority Data

Jan. 23, 1989 [JP] Japan .................................. 1-14528

[51] Int. Cl.$^5$ ........................ A61K 31/56; A61K 9/02
[52] U.S. Cl. .................................... 424/433; 424/430; 514/947; 514/967; 514/935
[58] Field of Search ............... 514/178, 967, 947, 935; 424/433, 430

[56] References Cited

U.S. PATENT DOCUMENTS

| | | | |
|---|---|---|---|
| 4,005,200 | 1/1977 | Utsumi et al. | 514/178 |
| 4,061,744 | 12/1977 | Sugimoto et al. | 514/178 |
| 4,496,556 | 1/1985 | Orentreich | 514/178 |
| 4,789,669 | 12/1988 | Sugimoto et al. | 514/178 |

*Primary Examiner*—Thurman K. Page
*Assistant Examiner*—Amy Hulina
*Attorney, Agent, or Firm*—Millen, White, Zelano & Branigan

[57] ABSTRACT

Disclosed is a vaginal suppository comprising a pharmaceutically acceptable salt of dehydroepiandrosterone sulfate (hereinafter referred to as DHAS), an amino acid and a hard fat having a hydroxy value of not more than 50. This suppository features an improved absorption of the active drug from the vagina plus a good shelf life.

17 Claims, No Drawings

VAGINAL SUPPOSITORY

This is a continuation of application Ser. No. 07/468,309 filed Jan. 22, 1990, now abandoned.

BACKGROUND OF THE INVENTION

1. Field of the Invention

The present invention relates to vaginal suppositories. More particularly, the invention relates to a vaginal suppository comprising a pharmaceutically acceptable salt of dehydroepiandrosterone sulfate (hereinafter referred to as DHAS), an amino acid and a hard fat having a hydroxy value of not more than 50.

Brief Description of the Prior Art

Some pharmaceutically acceptable salts of DHAS are known to increase the cervical ripeness at the terminal stage of pregnancy and potentiate the sensitivity to oxytocin of the uterine muscle, and clinically injections containing the sodium salt of DHAS have been frequently used as a drug which improves the state of the uterus preparatory to delivery.

Meanwhile, as an expedient dosage form, a vaginal suppository comprising a pharmaceutically acceptable salt of DHAS and a hard fat having a hydroxy value of not more than 50, which features an improved shelf life, has been disclosed in U.S. Pat. No. 4789669.

The inventors of the present invention did an assiduous research for improving the absorption of DHAS administered vaginally with due diligence and accomplished the present invention.

SUMMARY OF THE INVENTION

It is, therefore, an object of the invention to provide a vaginal suppository which assures an efficient absorption of DHAS.

Other objects and advantages of the invention will become apparent as the following description of the invention proceeds.

The finding which has culminated in the present invention is that the addition of a certain amino acid to a basal suppository composition comprising a pharmaceutically acceptable salt of DHAS and a hard fat having a hydroxy value of not more than 50 results in an enhanced systemic absorption of DHAS and an improvement in shelf life of the suppository.

DESCRIPTION OF THE PREFERRED EMBODIMENTS

Examples of the pharmaceutically acceptable salt of DHAS which is employed in the invention are the corresponding metal salts, such as salts with sodium, potassium, lithium, magnesium, etc. as well as the ammonium salt.

Examples of the amino acid to be employed are alanine, arginine, asparagine, aspartic acid, cysteine, cystine, glutamine, glutamic acid, glycine, histidine, hydroxylysine, hydroxyproline, isoleucine, leucine, lysine, methionine, ornithine, phenylalanine, proline, serine, threonine, tryptophan, tyrosine, valine and so on. Particularly preferred are glycine and L-arginine. These amino acids may be D- or L-configured or in the DL form. For the purposes of the invention, optionally two or more of these amino acids may be employed in combination.

The suppository base to be used in the present invention is a hard fat having a hydroxy value not exceeding 50. The term 'hard fat' means a mixture of glycerides whose constituent fatty acids are straight-chain saturated fatty acids of 8 to 18 carbon atoms, and examples of such hard fat are listed on Martindale The Extra Pharmacopeia, 28ed., p. 1067, London, The Pharmaceutical Press, 1982) and Standards for Ingredients of Drugs not in the Japanese Pharmacopeia Edited by Pharmaceutical Affairs Bureau, Ministry of Health and Welfare, Japan, p. 1239, Oct. 1, 1986, Yakugyo Jiho Co., Ltd., Tokyo, Japan). In the present invention, a hard fat with a hydroxy value of not more than 50 is employed. Such hard fats, with hydroxy values not exceeding 50, are available from commercial sources, for example under the trade names of Witepsol ® H-5, Witepsol ® H-15 and Witepsol ® H-35 (all from Dynamit Nobel Co.) and Nissan ® Pharmasol B-115 (Nippon Oil & Fats Co., Ltd).

The vaginal suppository according to the present invention is manufactured by melting a hard fat having a hydroxy value of not more than 50 under heating adding a pharmaceutically acceptable salt of DHAS and a suitable amino acid, mixing them evenly, pouring the composition into suppository molds in predetermined uniform quantities and cooling them.

The pharmaceutically acceptable salt of DHAS is preferably used in the form of a crystalline powder with a mean particle diameter in the range of 3 to 20 $\mu$m.

The proportion of said amino acid, based on each part by weight of the pharmaceutically acceptable salt of DHAS, is generally 0.2 to 3 parts by weight and preferably 0.25 to 2 parts by weight. The amino acid is preferably used in the form of finely divided powder with a mean particle diameter in the range of 5 to 25 $\mu$m.

The proportion of said hard fat with a hydroxy value of not more than 50, based on each part by weight of the pharmaceutically acceptable salt of DHAS, is generally 1 to 20 parts by weight and preferably 3 to 10 parts by weight.

The vaginal suppository according to the present invention is administered to pregnant women at 37 to 39 weeks of pregnancy, generally once to 3 times a day, the unit dose being 100 to 1500 mg as the pharmaceutically acceptable salt of DHAS.

The vaginal suppository of the invention is superior to the amino acid-free comparable vaginal suppository in the absorption of DHAS as shown in Test Example 1 given hereinafter. Furthermore, the vaginal suppository of the invention has an improved shelf life as demonstrated in Test Example 2 which also appears hereinafter.

The following test examples are illustrative of the usefulness of the vaginal suppository of the invention.

TEST EXAMPLE 1

Absorption test

1. Test materials

The under-mentioned vaginal suppositories were prepared according to the same formulas as given in Examples 1 to 6 and Control Example 1, which appear hereinafter, by the procedure set forth therein except that they were molded into 1.6 mm (dia.) cylindrical dosage forms for administration to rats.

Vaginal suppository A (according to the formula of Example 1)

Vaginal suppository B (according to the formula of Example 2)

Vaginal suppository C (according to the formula of Example 3)
Vaginal suppository D (according to the formula of Example 4)
Vaginal suppository E (according to the formula of Example 5)
Vaginal suppository F (according to the formula of Example 6)
Control vaginal suppository X (according to the formula of Control Example 1)

2. Test animals

Female Wistar rats at the terminal stage of pregnancy (mean body weight 220 g, primigravid, aged 13 weeks) were used in groups of 3 to 4 animals.

3. Method

Each test material equivalent to 4 mg of DHAS sodium per kg body weight was administered into the vagina of female rats fasted for 16 hours and the vaginal opening was closed up with a cyanoacrylate adhesive (Aron Alpha ®, Toagosei Chemical Industry Co., Ltd.) to prevent outflow of the drug. The rats were put back on feed 4 hours after administration. Immediately before administration and 1, 2, 3, 4, 6 and 8 hours after administration, the blood was collected through a cannula inserted into the jugular vein, heparinized and centrifuged at 10000 rpm for 5 minutes to separate the plasma. The DHAS in each plasma sample was assayed with a radioimmunoassay kit for DHAS ($^{125}$I-DHEA Sulfate Test, Wien Laboratories, Inc.) in accordance with the procedure set forth in the catalog (Catalog No. DS3300) and instruction manual accompanying the kit. Then, from the plasma DHAS concentration data for respective blood sampling times, the maximum plasma concentration ($C_{max}$) and the area under the plasma concentration-time curve ($AUC_{0-8h}$) were determined.

4. Results

The mean values in each treatment group are set forth in Table 1.

rial, the DHAS sodium and its degradation product dehydroepiandrosterone (DHA for short) in each test material were determined by high performance liquid chromatography (HPLC).

Determination of DHAS sodium and DHA

Three testpieces of each test material were sampled, pulverized and mixed, and about 0.8 g was accurately weighed (This quantity is designated as $W_T$). To this were added 20 ml of methanol and 5 ml of internal reference solution (a solution of butyl p-hydroxybenzoate in methanol, 0.8 mg/ml) and the mixture was warmed to 50° C. and shaken to dissolve the material. The solution was cooled to room temperature and centrifuged at 3000 rpm for 5 minutes and the supernatant was taken for use as a sample solution. On the other hand, about 0.1 g of DHAS sodium dihydrate was accurately weighed (the equivalent of this quantity as DHAS sodium anhydrate was designated as $W_S$). Similarly, about 0.02 g of DHA was accurately weighed (This quantity was designated as $W_D$) This quantity of DHA and the previously weighed DHAS sodium dihydrate were dissolved in methanol (20 ml)-internal reference solution (5 ml) to prepare a standard solution containing DHAS sodium and DHA hereinafter referred to as DHAS-DHA standard solution). Then, 5 μl of the sample solution and 5 μl of DHAS-DHA standard solution were respectively injected into a high performance liquid chromatograph.

HPLC parameter settings:
Apparatus : Shimadzu Liquid Chromatograph LC-5A (Shimadzu)
Detector : UV spectrophotometer (measuring wave length 214 nm)
Column : 4.6 mm (in dia.)×150 mm (length) end-capped octadecyl-bonded silica gel (5 μm) (Inertsil ® ODS, Gasukuro Kogyo Inc.)
Column temperature : room temperature
Mobile phase : methanol:0.02 M ammonium sulfate (68:32)
Flow rate : 1.0 ml/min.

TABLE 1

|  | Test sample | Amino acid Type | Amount* | $C_{max}$ (μg/ml) | $AUC_{0-8H}$ (μg·h/ml) |
|---|---|---|---|---|---|
| The invention | Vaginal suppository A | Glycine | 0.25 | 0.25 | 1.29 |
|  | Vaginal suppository B | Glycine | 0.5 | 0.42 | 2.01 |
|  | Vaginal suppository C | Glycine | 2.0 | 1.03 | 4.26 |
|  | Vaginal suppository D | DL-Alanine | 0.5 | 0.26 | 1.45 |
|  | Vaginal suppository E | L-Arginine | 0.5 | 0.44 | 2.07 |
|  | Vaginal suppository F | L-Aspartic acid | 0.5 | 0.34 | 1.64 |
| Control vaginal suppository X |  | Not added |  | 0.20 | 1.09 |

*Weight ratios to DHAS sodium

Thus, the vaginal suppositories containing various amino acids in accordance with the invention are superior to the amino acid-free control vaginal suppository in the absorption of DHAS from the vagina.

TEST EXAMPLE 2

Storage stability test

1. Test materials

The vaginal suppositories according to Examples 1 to 6.

2. Method

The stability test was conducted under accelerated aging conditions. Thus, ten pieces of each test material immediately after manufacture were allowed to stand at a constant temperature of 50° C. for 1 month and the appearance of each testpiece was then examined and the mean weight ($W_A$) of the testpieces was calculated. Then, to evaluate the storage stability of each test mate- The peak area ratio ($Q_S$) of DHAS sodium to internal reference (butyl p-hydroxybenzoate) after injection of DHAS-DHA standard solution and the peak area ratio $Q_T$) of DHAS sodium to internal reference (butyl p-hydroxybenzoate) after injection of the sample solution were respectively determined and the DHAS sodium content (C) per test material was calculated by means of the following equation.

$$C = W_S \times \frac{Q_T}{Q_S} \times \frac{W_A}{W_T}$$

From this (C) value and the DHAS sodium content ($C_i$) of the test sample immediately after manufacture as determined in the same manner as above, the percent residue of DHAS sodium after storage was calculated by means of the equation given below and, then, the mean value for each test material was calculated.

$$\text{Residue (\%)} = \frac{C}{C_i} \times 100$$

It should be understood that, in the above assay procedure, DHA is detected when it occurs at a level exceeding 0.4 mg per suppository. Actually, none of the test suppositories showed evidence of DHA.

2. Results

The test results are set forth in table 2.

TABLE 2

| Test sample | Amino Acid Type | Amount* | After 1 month of storage Appearance | % Residue of DHAS | DHA |
|---|---|---|---|---|---|
| Vaginal suppository of Example 1 | Glycine | 0.25 | White | 98.9 | N.D.** |
| Vaginal suppository of Example 2 | Glycine | 0.5 | White | 98.4 | N.D.** |
| Vaginal suppository of Example 3 | Glycine | 2.0 | white | 97.9 | N.D.** |
| Vaginal suppository of Example 4 | DL-Alanien | 0.5 | White | 100.1 | N.D.** |
| Vaginal suppository of Example 5 | L-Arginine | 0.5 | White | 99.2 | N.D.** |
| Vaginal suppository of Example 6 | L-Aspartic acid | 0.5 | White | 102.9 | N.D.** |

*Weight ratios of amino acids to DHAS sodium
**Not detected

It is apparent that the vaginal suppositories according to the invention are very satisfactory in storage stability.

EXAMPLES

Example 1

A stainless steel beaker was charged with 266.3 g of hard fat (Witepsol ® H-15, Dynamit Nobel Co.) and heated to 40°-42° C. to melt the fat. Then, 43.7 g of DHAS sodium dihydrate (average particle size 6 μm) and 10.0 g of glycine (average particle size 14 μm) were added and stirred to give a homogenous composition. This composition, maintained at 37°-38° C., was poured into spindle-shaped molds in portions of 1.6 g to give vaginal suppositories containing 200 mg of DHAS sodium and 50 mg of glycine per unit.

Example 2

A stainless steel beaker was charged with 256.3 g of hard fat (Witepsol ® H-15, Dynamit Nobel Co.) and heated at 40°-42° C. to melt the fat. Then, 43.7 g of DHAS sodium dihydrate (mean particle size 6 μm) and 20.0 g of glycine (mean particle size 14 μm) were added and stirred to give a homogenous composition. This composition, maintained at 37°-38° C., was poured into spindle-shaped molds in 1.6 g portions and cooled to give vaginal suppositories containing 200 mg of DHAS sodium and 100 mg of glycine per unit.

Example 3

The procedure of Example 1 was repeated except that the amounts of hard fat (Witepsol ® H-15, Dynamit Nobel Co.) and glycine were 196.3 g and 80.0 g, respectively. The procedure gave vaginal suppositories containing 200 mg of DHAS sodium and 400 mg of glycine per unit.

Examples 4 to 6

The procedure of Example 2 was repeated except that DL-alanine (mean particle size 22 μm), L-arginine (mean particle size 9 μm) or L-aspartic acid (mean particle size 18 μm) was used in lieu of glycine. The procedure gave vaginal suppositories containing 200 mg of DHAS sodium and 100 mg of DL-alanine per unit (Example 4), vaginal suppositories containing 200 mg of DHAS sodium and 100 mg of L-arginine per unit (Example 5), or vaginal suppositories containing 200 mg of DHAS sodium and 100 mg of L-aspartic acid per unit (Example 6).

Control Example 1

A stainless steel beaker was charged with 276.3 g of hard fat (Witepsol ® H-15, Dynamit Nobel Co.) and heated at 40-42° C to melt the fat. Then, 43.7 g of DHAS sodium dihydrate (mean particle size 6 μm) was added and stirred to give a homogenous composition. This composition, maintained at 37°-38° C., was poured into spindle-shaped molds and cooled to give vaginal suppositories containing 200 mg of DHAS sodium per unit.

What is claimed is:

1. A vaginal suppository comprising a pharmaceutically acceptable salt of dehydroepiandrosterone sulfate and, based on the weight of the salt, 0.2 to 3 parts by weight of an amino acid and 1 to 20 parts by weight of a hard fat having a hydroxy value of not more than 50.

2. A vaginal suppository according to claim 1 wherein said amino acid is at least one member selected from the group consisting of alanine, arginine, asparagine, aspartic acid, cysteine, cystine, glutamine, glutamic acid, glycine, histidine, hydroxylysine, hydroxyproline, isoleucine, leucine, lysine, methionine, ornithine, phenylalanine, proline, serine, threonine, tryptophan, tyrosine, valine and so on.

3. A vaginal suppository according to claim 1 wherein said amino acid is glycine or L-arginine or a mixture thereof.

4. A vaginal suppository according to claim 1 wherein said pharmaceutically acceptable salt of dehydroepiandrosterone sulfate is the sodium salt.

5. A vaginal suppository according to claim 1 wherein said pharmaceutically acceptable salt of dehydroepiandrosterone sulfate is a crystalline powder with a mean particle diameter of 3 to 20 μm.

6. A vaginal suppository according to claim 1, which contains 100 to 1500 mg of a pharmaceutically acceptable salt of dehydroepiandrosterone sulfate as a unit dose.

7. A vaginal suppository according to claim 1, wherein said pharmaceutically acceptable salt of dehydroepiandrosterone sulfate is the sodium salt in the form of a crystalline powder with a mean particle diameter of 3 to 20 μm, said suppository contains 100 to 1500 mg of dehydroepiandrosterone sulfate sodium salt, and said amino acid is glycine or L-arginine or a mixture thereof.

8. In a method of administering a pharmaceutically acceptable salt of dehydroepiandrosterone sulfate to a pregnant woman to promote maturation of the uterine cervix during late pregnancy to enhance the responsiveness of the uterine muscle to oxytocin, the improvement wherein the pharmaceutically acceptable salt is administered intravaginally at a dose of 100 to 1500 mg from one to 3 times daily, as a vaginal suppository according to claim 1.

9. A vaginal suppository comprising a pharmaceutically acceptable salt of dehydroepiandrosterone sulfate, 0.2 to 3 parts by weight, based on the weight of the salt of an amino acid, and a hard fat having a hydroxyl value of not more than 50.

10. A method for enhancing the transvaginal intake of dehydroepiandrosterone sulfate by a human subject from a vaginal suppository administered thereto which contains a pharmaceutically acceptable salt of dehydroepiandrosterone sulfate dispersed in a hard fat having a hydroxyl value of not more than 50, which comprises administering to said subject a vaginal suppository which contains 0.2 to 3 parts by weight of an amino acid based on the weight of the salt wherein the amount of amino acid is effective to enhance the transvaginal intake of the dehydroepiandrosterone sulfate.

11. A method of claim 10, wherein the suppository contains, based on the weight of the salt, 0.25 to 2 parts by weight of the amino acid and 3 to 10 parts by weight of the hard fat.

12. A method according to claim 10, wherein the amino acid is at least one member selected from the group consisting of alanine, arginine, asparagine, aspartic acid, cysteine, cystine, glutamine, glutamic acid, glycine, histidine, hydroxylysine, hydroxyproline, isoleucine, leucine, lysine, methionine, ornithine, phenylalanine, proline, serine, threonine, tryptophan, tyrosine, and valine.

13. A method according to claim 10, wherein the amino acid is glycine or L-arginine or a mixture thereof.

14. A method according to claim 10, wherein the pharmaceutically acceptable salt of dehydroepiandrosterone sulfate is the sodium salt.

15. A method according to claim 10, wherein the pharmaceutically acceptable salt of dehydroepiandrosterone sulfate is a crystalline powder with a mean particle diameter of 3 to 20 μm.

16. A method according to claim 10, wherein the vaginal suppository contains 100 to 1500 mg of a pharmaceutically acceptable salt of dehydroepiandrosterone sulfate as a unit does.

17. A method according to clam 10, wherein the pharmaceutically acceptable salt of dehydroepiandrosterone sulfate is the sodium salt in the form of a crystalline powder with a mean particle diameter of 3 to 20 μm, the suppository contains 100 to 1500 mg of dehydroepiandrosterone sulfate sodium salt, and the amino acid is glycine or L-arginine or a mixture thereof.

* * * * *